(12) United States Patent
Korneyev

(10) Patent No.: US 6,576,269 B1
(45) Date of Patent: Jun. 10, 2003

(54) TREATING OPEN SKIN LESIONS USING EXTRACT OF SEA BUCKTHORN

(76) Inventor: Alexander Y. Korneyev, 5308 Dutchman Dr., Raleigh, NC (US) 27606

( * ) Notice: Subject to any disclaimer, the term of this patent is extended or adjusted under 35 U.S.C. 154(b) by 0 days.

(21) Appl. No.: 09/947,576

(22) Filed: Sep. 6, 2001

(51) Int. Cl.$^7$ .............................................. A61K 35/78
(52) U.S. Cl. .................. 424/725; 424/777; 424/730; 424/765; 424/738; 424/764; 424/735; 424/757
(58) Field of Search .................. 424/725, 730, 424/738, 764, 765, 773, 774, 776, 777, 778

(56) References Cited

U.S. PATENT DOCUMENTS

| | | | |
|---|---|---|---|
| 4,956,354 A | * | 9/1990 | Gutierrez |
| 5,145,839 A | | 9/1992 | Beljanski ..................... 514/27 |
| 5,518,722 A | * | 5/1996 | Szaloki et al. |
| 5,738,850 A | * | 4/1998 | Hendricks et al. |
| 5,874,094 A | * | 2/1999 | Costello |
| 6,027,716 A | * | 2/2000 | Levin et al. |

FOREIGN PATENT DOCUMENTS

| | | | | |
|---|---|---|---|---|
| AU | 200125870 A | * | 7/2001 | |
| CN | 1260170 A | * | 7/2000 | |
| EP | 648496 A1 | * | 4/1995 | |
| GB | 2311009 B | * | 1/2000 | |
| HU | 56281 T | * | 8/1991 | |
| RU | 2097017 C1 | * | 11/1997 | |
| RU | 2129423 C1 | * | 4/1999 | |
| RU | 2144351 C1 | * | 1/2000 | |
| WO | WO 98/17297 | * | 4/1998 | |

OTHER PUBLICATIONS

Advertisement from Aubrey Products, www.smileherb.com, for "Sea Buckthorn Hand & Body Lotion".

* cited by examiner

Primary Examiner—Leon B. Lankford, Jr.
Assistant Examiner—Ruth Davis
(74) Attorney, Agent, or Firm—Richard D. Fuerle

(57) ABSTRACT

Disclosed is a method of preparing an extract of the herb sea buckthorn. In the absence of oxygen and metals berries of sea buckthorn are mixed with a vegetable oil and the mixture is incubated, which results in the extraction of liposoluble components of the berries into the vegetable oil. The extract is then separated from the berries. A composition is prepared of about 5 to about 95 wt % of the extract, 0 to about 95 wt % of an extract of a herb selected from the group consisting of rose hips (Rosa species), St. John's wort (*Hypericus perforatum*), chickweed herb (*Stellaria media*), plantain herb (*Plantago major*), calendula flowers (*Calendula officinalis*), and mixtures thereof, prepared by extracting liposoluble components of the herb into a vegetable oil in the absence of oxygen and metal, 0 to about 10 wt % of an essential oil, 0 to about 15 wt % of an antioxidant, and 0 to about 80 wt % of a diluent. The composition is applied to open skin lesions to promote their healing.

21 Claims, No Drawings

TREATING OPEN SKIN LESIONS USING EXTRACT OF SEA BUCKTHORN

BACKGROUND OF THE INVENTION

This invention relates to a method of extracting compounds from sea buckthorn, to compositions containing that extract, and to the use of those compositions to treat open skin lesions. In particular, it relates to extracting sea buckthorn in vegetable oil in the absence of metals and oxygen.

In 1998 there were over 33 million office visits to dermatologists in the United States, many due to open skin lesions. Elderly people, especially those in nursing facilities, are susceptable to open sores, also called bed sores, pressure ulcers, or decubitus ulcers, and there are an estimated three million pressure sores in the United States each year. For the past several decades, tens of billions of dollars have been spend caring for patients with pressure sores. Despite all of the knowledge generated, the treatment of pressure sores still requires several months, and they frequently become one of the main factors complicating a patient's life. One of the main functions of the skin is forming a barrier between the organism and the environment. Pressure sores and ulcers disrupt the integrity of the skin and open the gates for the bacterial penetration, leading to secondary infections and reducing life expectancy.

Bedsores are usually caused by reduced blood circulation in limited skin areas. Skin ulcers may be induced by long-term treatment with high doses of steroid hormones and occur as one of the side effects of chemotherapy and radiotherapy. Skin ulcers are one of serious complications of diabetes.

While primary damage may be inflicted by different causes, the healing of skin ulcers, traumatic wounds, burns and other open skin wounds and injuries usually undergo similar sequence of steps that results in restoration of structural integrity of the skin. These steps include wound cleansing, achieved through the influx of inflammatory cell, proliferation of stromal cells to initiate the restorative processes and ingrowth of blood vessels to provide nutritional support for the regeneration. Effective treatment may be expected to promote wound healing through the support of these steps and protection of the area of open injury against bacterial infection and dehydration.

Treatment of open skin sores in elderly patient is further complicated by the reduced rate of regenerative processes, decreased immune system activity, and increased sensitivity to antibiotic therapy. Therefore, topical preparations able to stimulate the regenerating ability of the skin and promote the healing process may assist the healing pressure sores, reduce the probability of secondary infections and improving the quality of patients life overall.

In spite of considerable advances in recent years in the treatment of burns and wounds, the occurrence of bedsores or decubitus ulcers continues to grow. Increases in the number of patients with restricted mobility, which most frequently suffer from bad sores and have the longest recovery period calls for the introduction of new, more efficient, and safe treatments. There are many different products available for the treatment of decubitus ulcers, mostly addressing the issues of prevention and elimination of the bacterial infection and protection against dehydration. Medications with potent antibacterial agents, such as antibiotics, iodine derivatives, hydrogen peroxide, boric acid derivatives etc. are good in protecting against infection, but the occurrence of allergic reactions and skin irritations to these agents may further reduce the rate of skin regeneration, increasing the recovery time, especially in the elderly patients. Medications, comprising synthetic antibacterial agent, hormones, or hormone derivatives, often induce skin sensitization during repetitive applications, usually required for successful treatment of decubitus ulcers. Administration of such medications on the daily basis may cause increasing skin irritation and inflammatory response, especially in elderly patients, interfering with the healing process.

It is a principal object of the present invention to overcome these disadvantages and provide a novel composition suitable for the treatment of open skin lesions, including bedsores or decubitus ulcers.

SUMMARY OF THE INVENTION

I have discovered that vegetable oil extracts of sea buckthorn, made in the absence of metals and oxygen, are superior to the same extracts made in the presence of metals or oxygen. Compositions made from the extract not only stimulate and provide the nutrients required for the proliferation of epithelial cells, but also protect the injured area against bacterial infections and dehydration over the course of treatment.

The present invention relates to the method and the compositions for the treatment of skin lesions, such as pressure sores or decubitus ulcers, heat burns, radiation and chemical burns, poor healing wounds and skin damages inflicted by laser or radiation therapy. The composition comprises liposoluble ingredients of sea buckthorn that provide nutrient and increases viability of regenerating cells. The composition may further include a combination of essential oils and herbal extracts, which stimulate regeneration of epidermal cells and have antibacterial properties. The composition is applied topically to the injured skin areas and as a result or repetitive administrations induces and stimulates restorative processes and promotes regeneration of the skin.

The present invention is related to the field of medical treatment of skin conditions, more specifically to a novel composition useful for the treatment and promotion of regeneration of open skin lesions. In particular but not exclusively the invention relates to compositions comprising liposoluble extract of sea buckthorn and its use in the treatment of pressure sores or decubitus ulcers and burns.

In brief, the composition according to the present invention is useful in the treatment of various open lesions of the skin, including open wounds, ulcers, burns, skin damages inflicted by radiation therapy or laser surgery, and in particular the composition is useful in the treatment of bedsores or decubitus ulcers. The composition is formulated as an ointment or lotion and is applied to the site of injury on the regular basis until the integrity of the skin surface is reconstituted. The composition includes liposoluble herbal extracts, essential oils, antioxidant, and vegetable oils. The liposoluble herbal extracts are present in the composition in the amount, which is effective to promote the regeneration of skin cells and provide nutritional support required for epithelial cell regeneration. Essential oils are included in the composition in the amount sufficient to stimulate cell regeneration and provide antibacterial action. Antioxidant is added to increase the stability of the composition and as a source of nutrients for regenerating skin cells. Vegetable oils are used a carrier or diluent and also protect the area of open skin injury against dehydration.

Another main object of this invention is to make available a novel composition useful in the continued and long-term treatment of bedsores or decubitus ulcers without skin sensitization, irritation or induction of adverse reactions of the skin.

A further objective of this invention is to provide a novel composition for the treatment of open skin lesions that stimulates tissue regeneration and promotes the restoration of skin integrity.

Other objective of the present invention is to provide a novel composition combining restorative action with protection against dehydration, and antiseptic effect.

Yet another objective of the present invention is to provide a method for the preparation of the composition for the treatment of open skin lesions.

DESCRIPTION OF THE PREFERRED EMBODIMENTS

In this invention an extract is made of the herb, sea buckthorn (*Hippophae rhamnoides*). A composition is made that includes the extract and the composition is used topically to treat open skin lesions.

Extraction

An extract is prepared of the berries of sea buckthorn using a vegetable oil as the solvent. The berries should be dried (humidity<12 wt %) as moisture interferes with the extraction. Examples of suitable vegetable oils that can be used for the extraction include almond oil, borage oil, canola oil, grape seed oil, jojoba oil, olive oil (virgin olive oil), soybean oil, sunflower oil, wheat germ oil, apricot kernel oil, and mixtures thereof. Olive oil is preferred because of its low viscosity, high stability, negligible occurrence of adverse skin reactions, and low cost. The amount of oil used should be about 2 to about 4 times the weight of ground herbs used; preferably, about 2.5 to about 3.5 times as much oil is used.

During the extraction, metal and oxygen are excluded because they degrade the extract and render it less effective. Metals can be excluded by performing the extraction in a container having a non-metallic internal surface, such as glass or plastic. To prevent the oxidation of the extract, the herbs to be extracted and the vegetable oil are placed in the container and the container is purged with an inert gas to remove the dissolved oxygen. This can be accomplished, for example, by sparging nitrogen into the vegetable oil. While extraction can be performed at room temperature, the mixture is preferably heated to between about 35° C. (95° F.) and about 65° C. (150° F.) with periodical shaking, to accelerate the extraction. After about 2 to about 4 days the extraction can be terminated.

The raw extract of liposoluble herbal ingredients is separated from the remaining herb. This can be accomplished, for example, by sedimentation for about 24 to about 48 hours at room temperature or by centrifugation at about 1000 g for about 30 to about 45 minutes at room temperature.

To obtain a higher concentration of the extract, the extraction cycle is preferably repeated 1 to 3 times, each time using the previously-obtained extract as the solvent. The final raw extract can be purified by filtering it at room temperature under a pressure of about 35 to about 200 psi through a series of filters having a pore size of about 8 mkm to about 0.45 mkm (micrometer).

The resulting liposoluble herbal extract is a mixture of many different compounds, some of which have not yet been identified. (Example 1 gives a typical analysis of some of the compounds in the extract.) These compounds are soluble in the vegetable oil, but are either insoluble in water or only slightly soluble in water. The compounds are also soluble in many organic solvents, such as hexane or ethyl acetate.

Other herbs used in the composition of this invention are extracted in the same manner. It is preferable to separately prepare extracts of each herb used, but the herbs can also be mixed and extracted together. If the herbs are extracted together, the mixture of herbs used in the extraction is preferably about 10 to about 50 wt % sea buckthorn and about 50 to about 90 wt % other herbs.

The Composition

The composition of the this invention includes about 5 to about 95 wt % of the liposoluble herbal extracts of sea buckthorn fruit, obtained in the absence of oxygen and metals. Less extract is less effective and more extract reduces the amount of other active components in the composition. Preferably, the composition contains about 15 to about 40 wt % of the sea buckthorn extract.

To further promote skin regeneration, the composition also preferably contains about 5 to about 95 wt %, and preferably about 15 to about 40 wt %, of the liposoluble herbal extract of at least one other herb. Examples of other herbs that can also be used include rose hips (Rosa species), St. John's wort (*Hypericus perforatum*), chickweed herb (*Stellaria media*), plantain herb (*Plantago major*), and calendula flowers (*Calendula officinalis*). Plantain is especially preferred as an additional herb for extraction. Generally, the plant itself or the leaves are used, but for rose hips, rose hips are used and for calendula the flowers are used.

To help promote healing and restorative processes, prevent infection, and inhibit inflammation, the composition also preferably includes about 0.01 to about 10 wt % (preferably about 1.0 to about 4.0 wt %) of at least one essential oil. Essential oils are volatile oils obtained from odoriferous plants. Examples of essential oils that can be used include bergamot (*Citrus bargamia*), cade (*Juniperus oxicedrus*), clove (*Eugenia cariophyllata*), frankincense (*Boswelia cartery*), geranium (*Pelargonium graveolence*), helichrysum (*Helichrisum angustifolium*), lavender (*Lavandula angustifolia, lavandula officinalis*), myrrh (*Commiphora myrrha*), niaouli (*Melaleuca viridiflora*), oregano (*Origanum vulgare*), palmarosa *Cymbopogon martini*), patchouli (*Pogostemon cablin*), rose (*Rosa damascena, Rosa mosqueta, Rosa centifolia*), rosewood (*Aniba rosaeodora*), sandalwood (*Santalum album*), tea tree oil (*Melaleuca alternifolia*), thyme (*Thymus vilgaris*), and ylang-ylang (*Cananga odorata*), and mixtures thereof. The preferred essential oils are helichrysum, palmarosa, frankincense, and geranium.

The composition also preferably contains an antioxidant, which increases the stability of the composition, protects the other ingredients from oxidation, and provides nutrients to support skin regeneration. The amount of antioxidant should be about 1 to about 15 wt %, as more antioxidant is unnecessary and less antioxidant is less effective; the preferred concentration of antioxidant is about 5 to about 10 wt %. Examples of antioxidants that can be used include natural tocopherols and tocotrienols, more specifically vitamin E-1000 IU oil, Vitamin E98 oil, palmvitee, natural vitamin E T-50 oil, and mixtures thereof. Vitamin E oil is the preferred antioxidant. Natural vitamin E oil (hereby referred to as Nat. vit. E), is a concentrate of natural mixed tocopherols in the oil form. Each gram of Natural vitamin E oil contains 500 mg of total tocopherols. The relative amounts of d-alpha, d-beta, d-gamma and d-delta tocopherols in the oil may vary to a certain extend, because of variability of the natural oil. At the same time, the following values, expressed as a percent of the total tocopherols, are typical: d-alpha—14%, d-beta—1%, d-gamma—62%, d-delta—23%.

The composition also preferably contains about 5 to about 80 wt % (preferably about 10 to about 40 wt %) of a diluent to reduce the concentration of the other components to change the viscosity of the composition and to support skin regeneration. The vegetable oils used in the extraction can be used as diluents, as can some other vegetable oils, including avocado oil, black currant oil, borage oil, carrot oil, coconut oil, cocoa butter, evening primrose oil, and mango butter. The preferred diluents are almond oil, carrot oil, or mixtures thereof.

The composition can be formulated as an oil, serum, ointment, lotion, or cream by using thinner or thicker oils in the extraction or as diluents. For example, increasing the percentage of avocado oil or jojoba oil will decrease the liquidity of the composition from an oil to a serum. Increasing the percentage of cocoa butter or coconut oil will further decrease liquidity to an ointment or cream.

Method of Treatment

Open skin lesions in humans or animals can be treated using a composition according to this invention by applying the composition to the area of the lesion. Examples of such open skin lesions include bed sores (decubitus ulcers), venous stasis ulcers, diabetic ulcers, traumatic wounds, poorly healing wounds, sun burns, heat burns, chemical burns, lacerations, and skin injury induced by radiation therapy or laser surgery. The area of the lesion is cleaned and the composition is applied to it once or twice a day until it has healed, which may require about 3 to about 8 weeks.

The following examples further illustrate this invention.

EXAMPLE 1

Commercially available dried sea buckthorn berries (humidity level of about 10%) in the amount of 6 lb were ground at room temperature using a hammer mill equipped with a 40 mesh (US std) screen. The ground material was mixed with 3 gallons of virgin olive oil in a 5-gallon glass container. The container with the mixture was purged with nitrogen for 20 minutes and closed with a cork. The container was placed in an incubator at a temperature of about 60° C. (140° F.) for 72 hours. The container was shaken manually every 2 to 3 hours during the daytime throughout the incubation. After the end of the incubation the container was left for 24 hours at room temperature to allow the oil layer to separate from the herbal material. The 1.8 gallons of the oil layer, called 1×raw extract, was collected by decantation. The 1×extract was mixed with a new ground plant material in a proportion of 1 pbw (part by weight) of plant material per 2 to 4 pbw of the extract and the procedure of extraction was repeated, including purging with nitrogen, incubation, and separation, to obtain a 2×extract.

The extraction cycle was repeated once more to obtain a 3×extract, the final raw extract. The final raw extract was purified by filtration at room temperature through paper filters, having a pore size of about 8 mkm, at a pressure of 40 psi to obtain liposoluble herbal extracts.

A typical composition for a sea buckthorn oil extract is presented in Table 1. In Table 1, the numbers after "C" are the number of carbon atoms in the fatty acid and the number of double bonds.

TABLE 1

| Ingredient | Concentration |
| --- | --- |
| Carotene (total) | 19500 IU/100 g |
| Beta-carotene | 12500 IU/100 g |
| Vitamin E | 47 mg/100 g |
| Fatty Acids: | |
| Arachidic acid (C20:0) | 0.64 g/100 g |
| Behenic acid (C22:0) | 0.25 g/100 g |
| Eicosenoic acid C20:1) | 1.13 g/100 g |
| Eicosadienoic acid C20:2) | 0.35 g/100 g |
| Erucic acid (C22:1) | 0.43 g/100 g |
| Heptadecenoic acid (C17:1) | 0.31 g/100 g |
| Lignoceric acid (C22:0) | 0.34 g/100 g |
| Linolenic acid (C18:3) | 4.90 g/100 g |
| Linoleic acid (C18:2) | 14.90 g/100 g |
| Margaric acid (C17:1) | 0.14 g/100 g |
| Myristic acid (C14:0) | 0.11 g/100 g |
| Myristoleic acid (C14:1) | 0.09 g/100 g |
| Oleic acid (C18:1) | 58.20 g/100 g |
| Palmitic acid (C16:0) | 10.30 g/100 g |
| Palmitoleic acid (C16:1) | 4.07 g/100 g |
| Pentadecenoic acid (C15:1) | 0.27 g/100 g |
| Stearic acid (C18:0) | 2.23 g/100 g |

(The analysis was conducted by Nutrition International Labs, Dayton, NJ.)

EXAMPLE 2

A sample (120 ml) of the extract prepared in Example 1 was placed in a tightly closed white glass vial and a sample (120 ml) of an identical extract prepared in the same manner but without excluding oxygen was placed in another tightly closed white glass vial. Both vials were kept in ambient light conditions at room temperature. After one year the amount of precipitate in the two vials was compared. The extract prepared in the presence of oxygen had a detectable amount of precipitate, while the extract prepared in Example 1 had virtually no precipitate. The presence of precipitate shows that the extract prepared in oxygen had degraded.

EXAMPLE 3

The procedure of Example 1 was repeated using various other herbs to obtain additional extracts. The extracts were standardized by measuring the optical density of the extract at the wavelengths corresponding to the absorption maximums (determined in preliminary experiments for each extract) and are presented in Table 2. The measurements were conducted using optical glass cuvettes with a 1 cm path length. Optical density was measured using the vegetable oil utilized for the extraction as a reference standard. Optical density was expressed in absorption units (ABS). According to the present invention, the liposoluble oil extract was considered acceptable for the manufacturing of the topical composition, if the optical density of the extract was equal or higher than the standard value obtained in the preliminary experiments and presented in the Table 2.

TABLE 2

| Extract | Wavelength (nm) | Optical Density (absorption units) | Reference standard | Dilution factor* |
| --- | --- | --- | --- | --- |
| Calendula | 439 | 0.56 | virgin olive oil | 1:4 |
| Calendula | 499 | 0.37 | " | 1:4 |
| Chickweed herb | 437 | 0.75 | " | undiluted |

TABLE 2-continued

| Extract | Wavelength (nm) | Optical Density (absorption units) | Reference standard | Dilution factor* |
|---|---|---|---|---|
| Chickweed herb | 483 | 0.62 | " | " |
| Plantain | 426 | 1.40 | " | " |
| Plantain | 507 | 0.30 | " | " |
| Rose hips | 440 | 0.62 | " | 1:4 |
| Rose hips | 507 | 0.58 | " | 1:4 |
| Sea buckthorn | 393 | 1.3 | " | undiluted |
| Sea buckthorn | 440 | 0.60 | " | 1:50 |
| St. John's wort | 390 | 0.44 | sweet almond oil | 1:4 |
| St. John's wort | 534 | 0.17 | " | undiluted |

*Oil extracts with optical density of more than 2.00 units at a given wavelength were diluted with hexane (HPLC grade). Reference standard was diluted with the same volume of hexane. Dilution factor shows how many volume of hexane were used per one volume of oil extract.

EXAMPLE 4

Various compositions were prepared using the extracts of Examples 1 and 3. The compositions were formed by adding the ingredients in oil form to a glass 120 ml bottle with a screw cap and mixing well. The compositions were stored at room temperature in amber glass vials with a tight cap. Tables 3a and 3b give the compositions in wt %. Compositions 1 to 10 in Table 3a are formulations of liposoluble herbal extracts and vegetable oils. Compositions 11 to 20 in Table 3b are preferred formulation of liposoluble oil extracts and essential oils.

TABLE 3a

| | Composition Number | | | | | | | | | |
|---|---|---|---|---|---|---|---|---|---|---|
| Component | 1 | 2 | 3 | 4 | 5 | 6 | 7 | 8 | 9 | 10 |
| Sea buckthorn | 45 | 45 | 45 | 45 | 45 | 12 | 12 | 12 | 12 | 15 |
| Nat. vit E | 5 | 5 | 5 | 5 | 5 | 5 | 5 | 5 | 5 | 5 |
| Grape seed | 5 | 5 | 5 | 5 | 5 | | | | | |
| Almond oil | 45 | | | | | 35 | | | | 10 |
| Chickweed | | 45 | | | | 12 | 12 | 12 | 12 | 15 |
| Plantain | | | 45 | | | 12 | 12 | 12 | 12 | 15 |
| Rose hips | | | | 45 | | 12 | 12 | 12 | 12 | 15 |
| St. John's wort | | | | | 45 | | | | | |
| Calendula | | | | | | 12 | | | | |
| Avacado oil | | | | | | | 35 | | | |
| Jojoba oil | | | | | | | | 35 | | |
| Carrot oil | | | | | | | | | | 10 |

TABLE 3b

| | Composition Number | | | | | | | | | |
|---|---|---|---|---|---|---|---|---|---|---|
| Component | 11 | 12 | 13 | 14 | 15 | 16 | 17 | 18 | 19 | 20 |
| Sea buckthorn | 15 | 15 | 15 | 15 | 15 | 15 | 15 | 15 | 15 | 15 |
| Chickweed | 15 | 15 | 15 | 15 | 15 | 10 | 10 | 10 | 10 | 10 |
| Plantain | 15 | 15 | 15 | 15 | 15 | 10 | 10 | 10 | 10 | 10 |
| Rose hips | 15 | 15 | 15 | 15 | 15 | 10 | 10 | 10 | 10 | 10 |
| Calendula | 15 | 15 | 15 | 15 | 15 | 10 | 10 | 10 | 10 | 10 |
| Nat. vit E | 5 | 5 | 5 | 5 | 5 | 5 | 5 | 5 | 5 | 5 |
| Carrot oil | 10 | 10 | 10 | 10 | 10 | 10 | 10 | 10 | 10 | 10 |
| Almond oil | 7 | 7 | 7 | 7 | 7 | | | 5 | 5 | 5 |
| Ylong-ylang | 3 | | | | | | | | | |
| Patchouli | | 3 | | | | | | | | |
| Palmarosa | | | 3 | | | | | | | |
| Helichrysum | | | | 3 | | | | 3 | 3 | 2 |
| Frankincense | | | | | 3 | | | | | |
| Coconut oil | | | | | | 27 | 25 | | | |
| Sandalwood | | | | | | 1 | | | | |
| Rose | | | | | | 1 | | | | |
| Oregano | | | | | | 1 | | | | |
| Rosewood | | | | | | | 2 | | | |
| Germanium | | | | | | | 2 | | | |
| Tea tree oil | | | | | | | 1 | | | 2 |
| Thyme | | | | | | | | 1 | | |
| Cade | | | | | | | | 1 | | |
| Myrrth | | | | | | | | | 1 | |
| Bergamot | | | | | | | | | 1 | |
| Niaouli | | | | | | | | | | 1 |

EXAMPLE 5

In this example, the effect of liposoluble herbal extracts on the proliferation of fibroblast-like cells in vitro were compared with that of virgin olive oil. Proliferation of fibroblasts in the wound area plays major role in the healing of cutaneous injuries, including sores, ulcers, and burns.

MPK cell line was obtained from American Type Culture Collection (ATCC). Cells were seeded at a density of $8 \times 10^4$ cells/well into 24 well plates with 1 ml Dulbecco's modified Eagle' medium, supplemented with 10% fetal calf serum, penicillin (100 U/ml) and streptomycin (0.1 mg/ml) per well and incubated at 37° C. After 24 hours of incubation, liposoluble herbal extracts or virgin olive oil were added in the amount 0.01 ml per cell in triplicates. Some cells were left without additives as a control. On day 4 cells were tripsinized, suspended in the medium and counted. The results, presented in the Table 4, are the average of 3 determinations and show that liposoluble herbal extracts of this invention stimulate the proliferation of fibroblast-like cells in cell culture. It should be mentioned that the presence of olive oil causes some reduction in cell count, possibly due to the adhesion of a portion of cells to the oil drops or to the interference of the oil drops with the cell counting. Assuming that the oil extract used for the test are made with an olive oil, the actual stimulating effect should be even higher than recorded.

TABLE 4

| Additives | Cell Count (cells/ml × $10^{-4}$) | Cell Count (% of control) |
|---|---|---|
| Control (no additives) | 44 | 100 |
| Olive oil | 36 | 82 |
| Sea buckthorn oil extract | 78 | 172 |
| Rose hip oil extract | 73 | 166 |
| Calendula oil extract | 41 | 93 |
| Plantain oil extract | 83 | 227 |
| Chickweed oil extract | 79 | 179 |
| St. John's oil extract | 37 | 75 |

EXAMPLE 6

In this example, the effect of topical Compositions 1 to 10, described in Table 3a, were compared on the model of the healing of traumatic transdermal wound in rats. These full thickness lesions in rats may simulate deep bed sore (decubitus ulcer) or diabetic ulcer in humans. Decubitus and diabetic ulcers frequently penetrate through the dermis and are often cleaned to remove necrotic tissue before the treatment. Therefore a deep wound bed is formed, similar, but not identical to full thickness dermal cuts in rats.

Male Sprague-Dawley rats (270 to 300 g) were housed individually under controlled conditions (21° C., 12 hours light/12 hours dark cycle starting at 7 AM) with food and water ad libitum for 1 week before use. A group of 5 animals was used for each composition. The rats were anesthetized with intraperitoneal injection of chloral hydrate 20 min prior to the surgery and the area behind the neck on the dorsal surface of the rats was shaved. Two 1.2×0.8 cm full thickness dermal wounds were cut 2.5 cm apart on both sides of the vertebra, about 2.5 cm behind the neck and left undressed. After the surgery the animals were placed back in their cage to recover from the anesthesia. The compositions under investigation were administered in the amount of 0.04 ml/dose first time 3 hours after the surgery and thereafter every day at 8–9 AM. Before the first administration 3.5 cm wide plastic collar was put around the neck of each animal, to prevent animal from leaking or scratching the wounds. Collars remained on animals during the whole period of observations. The compositions under investigation was administered to the wound on the right side of the animal and the vehicle (virgin olive oil) was administered to the wound on the left side of the animal at the same time. Thus the wound on the left side served as a control. Each composition and vehicle was administrated in the amount of 0.05 ml, sufficient to fully cover the wound area. The state of each wound was evaluated on $5^{th}$, $10^{th}$, $15^{th}$ and $20^{th}$ day by measuring the length of the wound and width of the wound in its widest part and estimating the area of the wound on each side of the animal. The areas of the wounds were expressed as the percent of the area of vehicle treated wound, measured on day 5 after the surgery (control wound area). Wound treatments were discontinued on the $15^{th}$ day after the surgery and the collars were removed at the same time. As shown in Table 5, wound closure was considerably accelerated when the test wounds were treated with the topical compositions under investigation relative to the test wounds treated with the vehicle. It can be concluded from this study that some compositions appear to be more efficient in promoting rat wound healing than others; however, it should be mentioned that these differences do not necessary predict their relative effectiveness in the treatment of human skin injuries. In Table 5, "S.E.M." means Standard Error of Mean.

TABLE 5

Wound Area (% of day 5 control wound area ± S.E.M.)

| Composition | After 5 days | After 10 days | After 15 days | After 20 days |
|---|---|---|---|---|
| Vehicle (control)* | 100 ± 7 | 76 ± 9 | 35 ± 7 | 8 ± 4 |
| 1 | 99 ± 8 | 61 ± 6 | 22 ± 5 | 4 ± 2 |
| 2 | 95 ± 10 | 53 ± 9 | 14 ± 7 | 2 ± 1 |
| 3 | 102 ± 10 | 51 ± 8 | 15 ± 4 | 2 ± 2 |
| 4 | 95 ± 9 | 57 ± 5 | 18 ± 4 | — |
| 5 | 104 ± 12 | 54 ± 11 | 23 ± 5 | 2 ± 2 |
| 6 | 97 ± 11 | 46 ± 7 | 19 ± 6 | 4 ± 2 |
| 7 | 96 ± 6 | 50 ± 12 | 11 ± 8 | — |
| 8 | 93 ± 8 | 48 ± 4 | 14 ± 5 | — |
| 9 | 101 ± 4 | 54 ± 7 | 20 ± 6 | 3 ± 3 |
| 10 | 98 ± 8 | 53 ± 8 | 8 ± 4 | — |

*The control wound area was measured on $5^{th}$ day after surgery in vehicle treated wounds.

EXAMPLE 7

A 10 year old male mixed breed dog experienced a traumatic wound to the right shoulder caused by a dog bite. The wound had been present for more than 4 months prior to the treatment. While part of the original wound healed within first two months, no progress in the healing of the remaining part was reported by the owned. At the time of the inspection an area of approx. 3.5 cm long and 1.0 cm wide was not healed. The treatment was conducted with preferred Composition 10 and consisted of administration of about 0.5 ml of the composition to the wound area by the animal's owner twice a day. The wound completely healed during 6 weeks of treatment.

EXAMPLE 8

A 4-year-old female German Sheppard dog suffered a chemical burn on her back as a result of accidentally spilled acid. While minor burns on her back healed, one large burned area of irregular shape and size about 6 cm long and 3 to 4 cm wide remained open for 3 months. The animal became agitated and unfriendly because of the constant pain and suffering. The treatment consisted of the application of Composition 10 to the wound with the aid of a sprayer. The composition was applied 3 to 4 times a day during the first two weeks. By the end of the second week the inflammation around the burn area was considerably reduced and the signs of healing and formation of a new skin on the edges of burn area became apparent. The composition was applied once per day for another week and then discontinued. The burn completely healed in 4 weeks.

EXAMPLE 9

An 81 year old woman had developed a decubitus ulcer on her left buttock. The ulcer was regularly cleansed and treated with several creams generally used to treat this type of lesion during 3 months period without significant improvement. By the time of inspection the size of the ulcer was 4 cm times 3.5 cm and approximately 2 cm deep with pockets reaching about 2 cm under the epidermis. After the cleansing with 3% hydrogen peroxide and drying with sterile napkin, the cavity of the ulcer was filled with Composition 17 (composition 17, Table 3) and covered with the bandage. The ulcer was dried with sterile absorbent cotton balls and Composition 17 was reapplied 12 hours later. The treatment was repeated twice per day during the first week, and once per day during next three weeks. The signs of improvement; closure of the subepidermal pockets, reduction and discontinuation of the exudates secretion, and disappearance of the bad odor, were noted during the second and third weeks of treatment. The ulcer reduced to a small skin lesion of about 1.5 times 1.5 cm with no measurable depth after 5 weeks and completely healed shortly thereafter.

EXAMPLE 10

A 75 year old man developed multiple bed sores (decubitus ulcers) on both buttocks and a bed sore on one elbow after staying in the bed for two months following the fracture of the leg. At the time of inspection there were two bed sores on the left buttock, one on the right buttock and one bedsore on the left elbow approximately 1.5 to 2 cm in diameter, with no visible pockets or areas of inflammation around the lesion and, according to the report of caretaker, they were growing in size. The two bedsores on the left buttock and one on the left elbow were treated with Composition 20. The bedsore on the right buttock was treated with topical cream containing Neosporin, which is generally used to treat similar types of skin lesions. Each treatment was applied twice per day during the first week and once a day thereafter. Clear signs of improvement, including the reduction of the bedsore size, reduction of the inflammation area around the bedsore, and the absence of exudates, were visible on the bedsores treated with Composition 20 during the second week of treatment. Two of the bedsores treated with Composition 20 healed during the third week of the treatment to the stage of formation of new skin and the third one healed to the same stage in the beginning of the fourth week. The bedsore on the right buttock, treated with the Neosporin cream, did not change the size by the end of the second week, though the inflammation area was practically invisible. Because of the difference in the progress of bedsores treated with Composition 20 and the Neosporin cream, the patient, on the advice of his caretaker, decided to change the treatment of the bedsore previously treated with Neosporin cream to Composition 20. The bedsore healed in next three weeks.

I claim:

1. A method of preparing an herbal extract comprising, in the absence of oxygen and metals,
   (A) forming a mixture of berries of sea buckthorn and a vegetable oil;
   (B) incubating said mixture whereby liposoluble components of said berries are extracted into said vegetable oil; and
   (C) separating said vegetable oil from said berries.

2. A method according to claim 1 wherein steps (A) to (C) are repeated at least once, each time using in step (A) the extract prepared in the previous steps.

3. A method according to claim 1 wherein said mixture is incubated at a temperature of about 35 to about 65° C. for about 2 to about 4 days.

4. A method according to claim 1 wherein said separating is performed at room temperature by sedimentation.

5. A method according to claim 1 wherein said separating is performed by centrifugation.

6. A method according to claim 1 wherein about 50 to about 90 wt %, based on the weight of said mixture, of an herb selected from the group consisting of rose hips, St. John's wort, chickweed herb, plantain herb, calendula flowers, and mixtures thereof, is mixed with said berries in step (A).

7. A method according to claim 1 wherein said vegetable oil is selected from the group consisting of almond oil, borage oil, canola oil, grape seed oil, jojoba oil, olive oil, soybean oil, sunflower oil, wheat germ oil, and mixtures thereof.

8. An extract obtained according to the method of claim 1.

9. A composition comprising
   (A) about 5 to about 95 wt %, of an extract according to claim 8;
   (B) 0 to about 95 wt % of an extract of a herb selected from the group consisting of rose hips, St. John's wort, chickweed herb, plantain herb, calendula flowers, and mixtures thereof, prepared by extracting liposoluble components of the herb into a vegetable oil in the absence of oxygen and metal;
   (C) 0 to about 10 wt % of an essential oil;
   (D) 0 to about 15 wt % of an antioxidant; and
   (E) 0 to about 80 wt % of a diluent.

10. A composition according to claim 9 wherein said essential oil is selected from the group consisting of essential oils of bergamot, cade, clove, frankincense, geranium, helichrysum, lavender, lavandula, myrrh, niaouli, oregano, palmarosa, patchouli, rose, rosewood, sandalwood, tea tree oil, thyme, ylang-ylang, and mixtures thereof.

11. A composition according to claim 9 said diluent is selected from the group consisting of almond oil, borage oil, canola oil, grape seed oil, jojoba oil, olive oil, soybean oil, sunflower oil, wheat germ oil, apricot kernel oil, carrot oil, coconut oil, cocoa butter, mango butter, evening primrose oil, black currant oil, avocado oil, and mixtures thereof.

12. A composition according to claim 9 formulated as an oil, serum, ointment, lotion, or cream for topical application.

13. A composition according to claim 9 wherein said anti-oxidant is vitamin E.

14. A method of treating an open skin lesion comprising applying a composition according to claim 9 to said lesion.

15. A composition comprising
   (A) about 5 to about 95 wt % of an extract according to claim 8;
   (B) 5 to about 95 wt % of an extract of a herb selected from the group consisting of rose hips, St. John's wort, chickweed herb, plantain herb, calendula flowers, and mixtures thereof, prepared by extracting liposoluble components of the herb into a vegetable oil in the absence of oxygen and metal;
   (C) 0.01 to about 10 wt % of an essential oil;
   (D) 1 to about 15 wt % of an antioxidant; and
   (E) 5 to about 80 wt % of a diluent.

16. A method of preparing an extract comprising, in the absence of oxygen and metals,
   (A) preparing a mixture, in a non-metallic container, of dried sea buckthorn berries and about 2 to about 4 pbw per pbw of said berries of a vegetable oil selected from the group consisting of almond oil, borage oil, canola oil, grape seed oil, jojoba oil, olive oil, soybean oil, sunflower oil, avocado oil, carrot oil, coconut oil, wheat germ oil, and mixtures thereof;
   (B) purging said mixture of dissolved oxygen;
   (C) incubating said mixture at the temperature of about 35° C. to about 65° C. for a time sufficient to form an extract of liposoluble herbal components from said berries;
   (D) separating said extract from said berries; and
   (E) repeating steps (A) to (D) at least once, each time using in step (A) the extract obtained from the previous steps.

17. A composition comprising
   (A) about 5 to about 95 wt % of an extract prepared according to the method of claim 16;
   (B) about 5 to about 95 wt % of an extract of a herb selected from the group consisting of rose hips, St. John's wort, chickweed herb, plantain herb, calendula flowers, and mixtures thereof, prepared by extracting said herb in a vegetable oil in the absence of oxygen and metal;
   (C) about 0.01 to about 10 wt % of an essential oil selected from the group consisting of bergamot, cade, clove, frankincense, geranium, helichrysum, lavender, myrrh, niaouli, oregano, palmarosa, patchouli, rose, rosewood, sandalwood, tea tree oil, thyme, ylang-ylang, and mixtures thereof;
   (D) about 1 to about 15 wt % of an antioxidant; and
   (E) about 5 to about 80 wt % of a diluent.

18. A method of treating an open skin lesion comprising applying a composition according to claim 17 to said lesion.

19. A method of preparing an extract comprising
   (A) in a glass container placing a mixture of dried berries of sea buckthorn and about 2 to about 4 pbw per pbw of said berries of olive oil, and mixtures thereof;

(B) sparging nitrogen through said mixture to remove dissolved oxygen;

(C) incubating said mixture at the temperature of about 35° C. to about 65° C. for about 2 to about 4 days to form an extract of liposoluble herbal components from said berries;

(D) separating said extract from said berries;

(E) repeating steps (A) to (D) 1 to 3 times, each time using in step (A) the extract obtained from the previous steps; and (F) filtering the extract.

20. A composition comprising (A) about 15 to about 40 wt % of an extract according to claim 19;

(B) about 15 to about 40 wt % of an extract of plantain, prepared by extracting in a vegetable oil in the absence of oxygen and metal;

(C) about 1.0 to about 4.0 wt % of an essential oil selected from the group consisting of helichrysum, palmarosa, frankincense, geranium, and mixtures thereof;

(D) about 5 to about 10 wt % vitamin E; and (E) about 10 to about 40 wt % of a diluent selected from the group consisting of almond oil, carrot oil, or mixtures thereof.

21. A method of accelerating the healing in animals and humans of open skin lesions selected from the group consisting of decubitus ulcers, venous stasis ulcers, diabetic ulcers, traumatic wounds, poorly healing wounds, sun burn, heat burn, chemical burn, lacerations, and skin injuries induced by radiation therapy or laser surgery comprising applying a composition according to claim 20 to said lesion.

* * * * *